United States Patent
Yonehara et al.

(10) Patent No.: US 6,790,665 B2
(45) Date of Patent: Sep. 14, 2004

(54) METHOD OF QUANTIFYING HEMOGLOBIN AND METHOD OF MEASURING GLYCATION RATIO OF HEMOGLOBIN

(75) Inventors: Satoshi Yonehara, Kyoto (JP); Yuji Yagi, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/380,961

(22) PCT Filed: Sep. 27, 2001

(86) PCT No.: PCT/JP01/08482
§ 371 (c)(1),
(2), (4) Date: Mar. 20, 2003

(87) PCT Pub. No.: WO02/27330
PCT Pub. Date: Apr. 4, 2002

(65) Prior Publication Data
US 2003/0186449 A1 Oct. 2, 2003

(51) Int. Cl.$^7$ .............................................. G01N 33/72
(52) U.S. Cl. ........................... 436/66; 436/67; 436/164; 436/904
(58) Field of Search ............................ 436/66, 67, 164, 436/166, 904; 422/82.05, 82.09

(56) References Cited

U.S. PATENT DOCUMENTS

| | | | |
|---|---|---|---|
| 5,902,731 A | * 5/1999 | Ouyang et al. | 435/26 |
| 5,955,027 A | 9/1999 | Kosaka | 422/56 |
| 5,985,591 A | * 11/1999 | Yonehara et al. | 435/28 |
| 6,352,835 B1 | 3/2002 | Komori et al. | 435/25 |
| 6,514,720 B2 | * 2/2003 | Komori et al. | 435/25 |
| 2002/0025546 A1 | * 2/2002 | Komori et al. | 435/28 |
| 2003/0162242 A1 | * 8/2003 | Yonehara | 435/25 |

FOREIGN PATENT DOCUMENTS

| | | |
|---|---|---|
| JP | 60-227171 | 11/1985 |
| JP | 2-184758 | 7/1990 |
| JP | 2000-093197 | 4/2000 |

* cited by examiner

*Primary Examiner*—Maureen M. Wallenhorst
(74) *Attorney, Agent, or Firm*—Merchant & Gould P.C.

(57) ABSTRACT

A method of determining Hb is provided, by which an amount of Hb can be determined easily and accurately without fear of damage to the environment. Hemoglobin in a sample is denatured with a tetrazolium compound to give denatured hemoglobin, and an amount of an optical change in the sample is measured at an absorption wavelength specific to the denatured hemoglobin. Using the amount of the optical change thus measured, an amount of the hemoglobin in the sample can be determined. The amount of the optical change preferably is measured at a wavelength in a range from 520 to 670 nm. According to this method, an amount of Hb can be determined with high accuracy as shown in FIG. 1.

22 Claims, 1 Drawing Sheet

METHOD OF QUANTIFYING HEMOGLOBIN AND METHOD OF MEASURING GLYCATION RATIO OF HEMOGLOBIN

TECHNICAL FIELD

The present invention relates to a method of determining an amount of hemoglobin (Hb) in a sample.

BACKGROUND ART

Hb in the blood plays an important role in transporting oxygen from the lungs to organs and thus relates to diseases such as leukemia, anemia, and the like, for example. Therefore, determining an amount of Hb has been considered very important in the field of a clinical analysis. On the other hand, glycated Hb serves as an important index for the diagnosis, treatment, etc. of diabetes because it reflects previous blood glucose levels in vivo. Therefore, determining a ratio of glycated Hb also has been considered important. For determining the ratio of glycated Hb, it is necessary to determine the amount of Hb.

Examples of a method of determining Hb include measuring an absorbance of Hb. However, the Hb that is not yet denatured (hereinafter, referred to as "undenatured Hb") exhibits an absorption maximum at different wavelengths depending on its state, e.g., the state where it is bound to oxygen, the state where it is not bound to oxygen, etc. Therefore, it is difficult to determine an amount of Hb accurately by merely measuring the absorbance of the Hb. On this account, conventionally, a method has been employed in which the absorbance of Hb is measured after the Hb has been denatured so as to be stabilized. Examples of such a method include a cyanmethemoglobin method (HiCN method), azide metohemoglobin method, sodium lauryl sulfate method (SLS method), alkaline hematin method, and the like. Among these, the HiCN method, which is an international standard method, is employed particularly widely. In this HiCN method, a reagent containing potassium ferricyanide and potassium cyanide is added to blood so that Hb is converted into stable cyanmethemoglobin, and the absorbance is measured at a predetermined wavelength (540 nm) to determine the amount of the Hb.

DISCLOSURE OF INVENTION

However, the HiCN method and the azide metohemoglobin method are not preferable from the viewpoint of environmental friendliness because the HiCN method produces a toxic liquid waste containing a cyanogen compound and the azide metohemoglobin method produces a liquid waste containing sodium azide. Further, the SLS method and the alkaline hematin method have the following problem. In these methods, a reagent such as SLS and a strong alkali is added to a sample as a protein-denaturing agent. Thus, when the sample containing such a reagent is used directly for the determination of a substance other than Hb, the reagent affects the system of determination utilizing an enzyme and the like, for example, which makes the determination difficult. Therefore, with respect to the sample that has been subjected to the treatment for denaturing Hb, it is difficult to carry out the determination of the denatured Hb and the determination of the substance other than the denatured Hb in a series of operations.

Therefore, it is an object of the present invention to provide a method of determining Hb, by which an amount of Hb can be determined easily and accurately without fear of damage to the environment.

In order to achieve the above object, a method of determining Hb according to the present invention includes: denaturing Hb in a sample with a tetrazolium compound to give denatured Hb; measuring an amount of an optical change in the sample at an absorption wavelength specific to the denatured Hb; and calculating an amount of the Hb in the sample from the amount of the optical change. The term "denatured Hb" as used in the present invention refers to Hb that has been denatured with a tetrazolium compound.

While the undenatured Hb exhibits various absorption wavelengths depending on its state, the denatured Hb obtained by the treatment with the tetrazolium compound is stable and exhibits the absorption maximum at a wavelength falling within a certain range. Therefore, according to the method of determining Hb of the present invention, an amount of Hb can be determined easily. In addition, the method of the present invention does not use a cyanogen compound, a strong alkali, or the like as used in the above-mentioned conventional methods. Therefore, the method of the present invention is a useful method without fear of damage to the environment.

In the method of determining Hb according to the present invention, the amount of the optical change may be an absorbance, reflectance, or the like, for example.

The tetrazolium compound is not specifically limited. For example, tetrazolium compounds described later can be used. Among these, 2-(4-iodophenyl)-3-(2,4-dinitrophenyl)-5-(2,4-disulfophenyl)-2H-tetrazolium salt (e.g., available from Dojindo Laboratories under the trade name WST-3) is most preferable.

In the method of determining Hb according to the present invention, the wavelength for measuring the denatured Hb preferably is in the range from 440 to 700 nm, more preferably from 500 to 670 nm, and most preferably 540 to 670 nm.

In the method of determining Hb according to the present invention, the amount of the tetrazolium compound added to the sample is not specifically limited and can be decided as appropriate depending on the type of the sample and the like. More specifically, it is preferable that the tetrazolium compound is added to the sample so that a content of the tetrazolium compound per microliter of the sample is in the range from 0.001 to 100 µmol, more preferably from 0.01 to 10 µmol, and most preferably from 0.05 to 5 µmol, for example.

The sample is not specifically limited. However, as described later, a sample containing red blood cells, e.g., whole blood, preferably is used. In the case where the sample is whole blood, the tetrazolium compound preferably is added to the sample so that a content of the tetrazolium compound per microliter of the sample is in the range from 0.01 to 30 µmol, more preferably from 0.05 to 10 mol, and most preferably from 0.1 to 5 µmol, for example. In general, it is estimated that whole blood contains about 50 vol % of blood cells.

In the method of determining Hb according to the present invention, it is preferable that the Hb in the sample is treated with the tetrazolium compound in the presence of a surfactant. When the surfactant is present in addition to the tetrazolium compound, denaturation of the Hb can be accelerated still further so that the Hb can be determined quickly.

In the method of determining Hb according to the present invention, the amount of the surfactant added to the sample is not specifically limited, and can be decided as appropriate, for example, depending on the amount of the tetrazolium compound added to the sample and the like. More specifically, the surfactant is added to the sample so that a content of the surfactant per mole of the tetrazolium compound is in the range from 0.01 to 70 mol, preferably from 0.05 to 50 mol, and more preferably from 0.1 to 20 mol.

In the method of determining Hb according to the present invention, the sample is not specifically limited and can be, for example, blood samples such as whole blood, plasma, serum, blood cells, and the like. It is preferable to use a sample containing red blood cells, for example, a whole blood sample, a blood cell sample, etc.

Next, a method of determining a ratio of glycated Hb according to the present invention includes: determining an amount of Hb in a sample containing glycated Hb by the method of determining Hb according to the present invention; causing a redox reaction between a glycation site of the denatured Hb obtained and a fructosyl amino acid oxidase (hereinafter, referred to as "FAOD"); determining the redox reaction to determine an amount of the glycated Hb; and calculating a ratio of the glycated Hb from the amount of the Hb and the amount of the glycated Hb. It is to be noted here that the amount of Hb refers to the amount of both the glycated Hb and the Hb that is not glycated.

Similarly to the method of determining Hb described above, the method of determining a ratio of glycated Hb according to the present invention also produces no toxic liquid wastes. Therefore, the method of determining a ratio of glycated Hb according to the present invention also is a useful method without fear of damage to the environment. In addition, unlike the strongly alkaline reagent and the like as described above, the tetrazolium compound does not have any effect, such as deactivation of an enzyme, on the determination of the amount of glycated Hb by the enzymic method utilizing the redox reaction. Accordingly, the determination of the Hb as described above and the determination of the amount of the glycated Hb can be carried out simply in a series of operations using the sample treated with the tetrazolium compound. Therefore, the determination of the ratio of glycated Hb according to the present invention can be carried out, for example, utilizing only one reaction system using a single measuring apparatus. Moreover, the tetrazolium compound added to the sample not only can denature the Hb but also can eliminate the effect of a reducing substance present in the sample on the redox reaction. Therefore, the ratio of glycated Hb can be determined with higher accuracy.

In the method of determining a ratio of glycated Hb according to the present invention, the wavelength for measuring the denatured Hb preferably is in the range from 440 to 700 nm, more preferably from 500 to 670 nm, and most preferably 540 to 670 nm as described above.

In the method of determining a ratio of glycated Hb according to the present invention, it is preferable that determining the redox reaction is measuring an amount of an optical change in a color-developing substance produced by the redox reaction. As described above, the amount of the optical change may be an absorbance, reflectance, or the like, for example.

In the enzymic method as described above, in general, dual-wavelength measurement dominantly is used for measuring the amount of the optical change. The dual-wavelength measurement is carried out, for example, in the following manner. First, an absorbance of a substance to be measured (e.g., a color-developing substance) is measured at a main wavelength at which the substance exhibits an absorption maximum. Then, at a sub-wavelength that is different from the main wavelength, electrical noises, cloudiness of the sample, changes in the amount of light, etc. are measured to correct the measured value obtained at the main wavelength. Therefore, it is preferable that the sub-wavelength is a wavelength at which a substance other than the substance to be measured (the color-developing substance) present in the sample exhibits no absorption. The main wavelength is decided as appropriate depending on the absorption wavelength of the substance to be measured. In general, the main wavelength is in the range from about 650 to 800 nm. In this case, the sub-wavelength is set to be higher than the main wavelength, e.g., in the range from about 800 to 900 nm. However, as described above, the undenatured Hb is unstable and exhibits absorption at various wavelengths depending on its state, e.g., the state where it is bound to oxygen, the state where it is not bound to oxygen, etc. Thus, in the case where the amount of the glycated Hb is determined, for example, by measuring the absorbance of the color-developing substrate and the like, the Hb exhibits absorption also at the sub-wavelength, which makes it difficult to determine the amount of the glycated Hb accurately. In contrast, the wavelength for measuring the denatured Hb obtained by the treatment with the tetrazolium compound is as described above. Therefore, even when the sub-wavelength in the determination of the amount of glycated Hb is set in the range from 800 nm to 900 nm, for example, the effect of the absorption by the unstable undenatured Hb, which exhibits absorption at various wavelengths depending on its state, is not observed. As a result, the amount of the glycated Hb can be determined with higher accuracy.

A wavelength for measuring the color-developing substance is in the range from 500 to 800 nm, preferably from 540 to 750 nm, for example.

Further, as described later, a wavelength for measuring the color-developing substance may be the same as that for measuring the amount of the Hb. In this case, the wavelength preferably is in the range from 500 to 670 nm, more preferably from 540 to 670 nm.

In the method of determining a ratio of glycated Hb according to the present invention, it is preferable that the denatured Hb is treated with a protease before causing the redox reaction between the glycation site of the denatured Hb and the FAOD. The FAOD acts on a glycated amino acid and a glycated peptide fragment shorter than a glycated protein and a glycated peptide more easily than on the glycated protein and the glycated peptide. On this account, the denatured Hb is degraded with a protease in advance so that the FAOD can act on the glycation site of the denatured Hb more easily, thereby allowing the accuracy of determination to be improved.

As described above, by using the method of determining Hb according to the present invention, it becomes possible to use the sample that has been subjected to the treatment for denaturing Hb directly for the determination of the amount of the glycated Hb. Therefore, the determination of the amount of the Hb and the determination of the amount of the glycated Hb can be carried out, for example, in the following orders.

For example, a first method of determining a ratio of glycated Hb is a method in which the redox reaction is caused between the glycation site of the denatured Hb and the FAOD after the amount of the optical change in the sample is measured at the absorption wavelength specific to the denatured Hb.

In the case where a protease treatment is carried out in this first method, the method may be carried out in such a manner that the amount of the optical change in the sample is measured at the absorption wavelength specific to the denatured Hb, the denatured Hb is then treated with a protease, and thereafter, a redox reaction is caused between a glycation site of a degradation product of the denatured Hb and FAOD. Alternatively, the method may be carried out in such a manner that the denatured Hb is treated with a protease, the amount of the optical change in the sample is then measured at the absorption wavelength specific to the denatured Hb, and thereafter, a redox reaction is caused between a glycation site of a degradation product of the denatured Hb and FAOD.

On the other hand, for example, a second method of determining a ratio of glycated Hb is a method in which, after the redox reaction is caused between the glycation site of the denatured Hb and the FAOD, the amount of the optical change in the sample is measured at the absorption wavelength specific to the denatured Hb and the redox reaction is determined. In the case where the second method is employed, by measuring the denatured Hb and the color-developing substance at the wavelengths different from each other, it becomes possible to determine the amount of the optical change in both the denatured Hb and the color-developing substance at the same time.

In the case where a protease treatment is carried out in this second method, the denatured Hb may be treated with a protease before the redox reaction is caused between the glycation site of the denatured Hb and the FAOD, for example.

In the method of determining a ratio of glycated Hb according to the present invention, it is preferable that the amount of the optical change in the color-developing substance corresponds to an amount of hydrogen peroxide generated by the redox reaction between the glycation site of the denatured Hb and the FAOD. Further, it is preferable that the color-developing substance is a substrate that develops color by oxidation (hereinafter, referred to as a color developing substrate) and has developed color as a result of a reaction caused by an oxidase between the hydrogen peroxide and the substrate.

The oxidase is not specifically limited. However, POD preferably is used as the oxidase. Also, the color-developing substrate is not specifically limited. However, N-(carboxymethylaminocarbonyl)-4,4'-bis(dimethylamino) diphenylamine sodium (e.g., available from Wako Pure Chemical Industries, Ltd. under the trade name DA-64), for example, preferably is used as the color-developing substrate because it can be detected with high sensitivity.

The sample used in the method of determining a ratio of glycated Hb according to the present invention is not specifically limited. Examples of the sample include those described above.

BEST MODE FOR CARRYING OUT THE INVENTION

Figure 1:
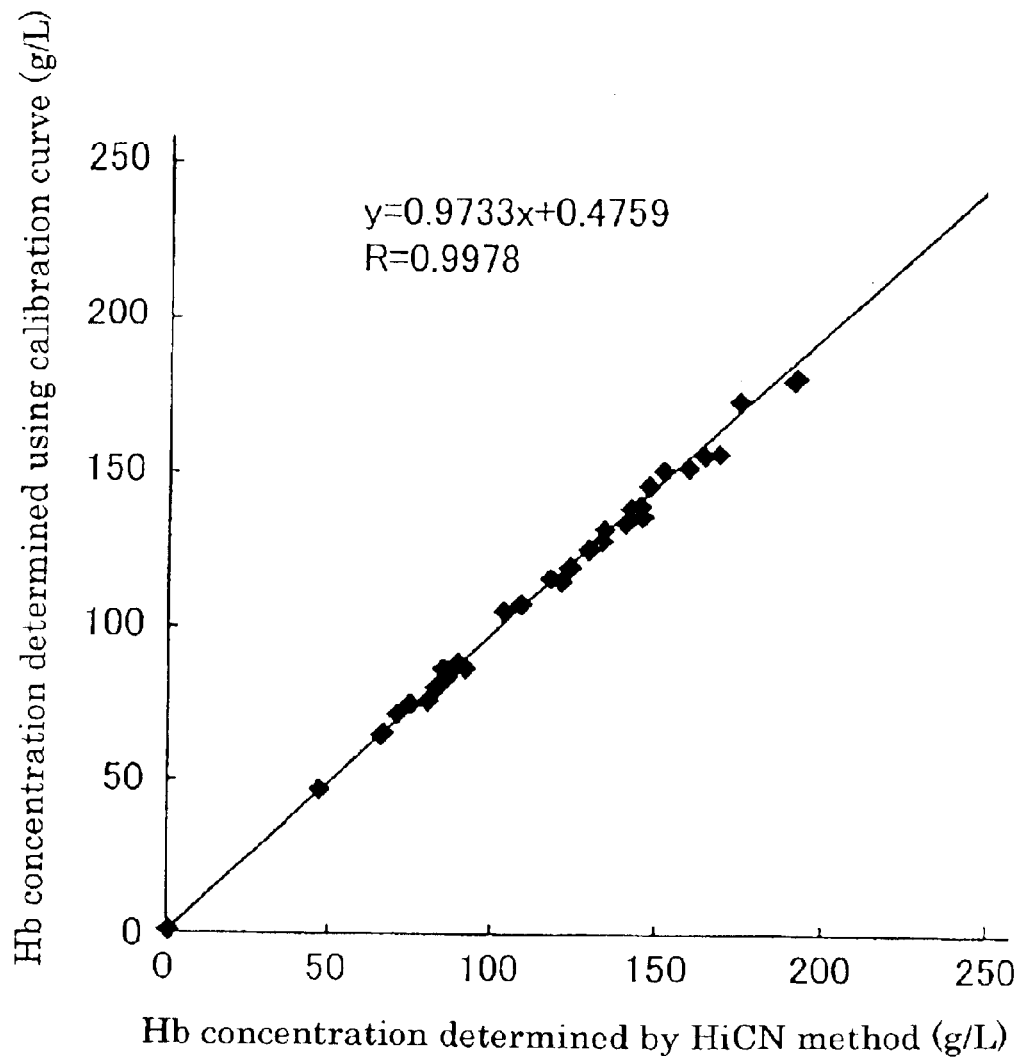
FIG. 1 is a graph showing the correlation between a Hb concentration determined by the method of determining Hb according to one example of the present invention and a Hb concentration determined by a control method.

The tetrazolium compound to be used in a method of determining Hb according to the present invention prefer-ably contains ring substituents at least at two positions on its tetrazole ring, more preferably at three positions on its tetrazole ring, for example.

In the case where the tetrazolium compound contains ring substituents at least at two positions on its tetrazole ring as described above, it is preferable that the ring substituents are at the 2-position and 3-position on the tetrazole ring. Further, in the case where the tetrazolium compound contains ring substituents at three positions on its tetrazole ring, it is preferable that the ring substituents are at the 2-position, 3-position, and 5-position on the tetrazole ring.

Further, it is preferable that at least two ring substituents of the tetrazolium compound have a benzene ring structure. Other than the benzene ring structure, the ring substituents may have a resonance structure with S or O being contained in the ring skeleton, for example. Examples of the ring substituents with such a resonance structure include a thienyl group, thiazoyl group, and the like.

Furthermore, it is preferable that the tetrazolium compound contains ring substituents at least at three positions on its tetrazole ring and at least two of the ring substituents have a benzene ring structure.

Still further, it is preferable that at least one ring substituent contains a functional group, and a larger number of functional groups are more preferable.

As the functional group, an electron-withdrawing functional group preferably is used. For example, a halogen group, ether group, ester group, carboxy group, acyl group, nitroso group, nitro group, hydroxy group, sulfo group, and the like can be used. Other than these, characteristic groups containing oxygen such as a hydroperoxy group, oxy group, epoxy group, epidioxy group, oxo group, and the like; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, isothiocyanate group, and the like also can be used, for example. Among these electron-withdrawing functional groups, a nitro group, sulfo group, halogen group, carboxy group, hydroxy group, methoxy group, ethoxy group are preferable. Further, in addition to the above-mentioned electron-withdrawing functional groups, unsaturated hydrocarbon groups such as a phenyl group ($C_6H_5$—), styryl group ($C_6H_5CH=CH$—), and the like also can be used, for example. It is to be noted that the functional groups may have been ionized by dissociation.

Still further, it is preferable that the tetrazolium compound contains benzene rings at the 2-position and 3-position on its tetrazole ring and at least one of the benzene rings contains at least one functional group selected from the group consisting of a halogen group, carboxy group, nitro group, hydroxy group, sulfo group, methoxy group, and ethoxy group. It is to be noted here that both the benzene rings may contain the functional group. Further, the functional group may be contained at any positions (ortho-, meta-, para-) on the benzene ring. Furthermore, the number of the functional group is not specifically limited, and in the case where the at least one of the benzene rings contains a plurality of functional groups, the functional groups contained in the benzene ring may be the same or different.

Examples of the tetrazolium compound containing ring substituents having a benzene ring structure at the 2-position, 3-position, and 5-position on its tetrazole ring include:

2-(4-iodophenyl)-3-(4-nitrophenyl)-5-(2,4-disulfophenyl)-2H-tetrazolium salt;

2-(4-iodophenyl)-3-(2,4-dinitrophenyl)-5-(2,4-disulfophenyl)-2H-tetrazolium salt;

2-(2-methoxy-4-nitrophenyl)-3-(4-nitrophenyl)-5-(2,4-disulfophenyl)-2H-tetrazolium salt;

2-(4-iodophenyl)-3-(4-nitrophenyl)-5-phenyl-2H-tetrazolium salt;

3,3'-(1,1'-biphenyl-4,4'-diyl)-bis(2,5-diphenyl)-2H-tetrazolium salt;

3,3'-[3,3'-dimethoxy-(1,1'-biphenyl)-4,4'-diyl]-bis[2-(4-nitrophenyl)-5-phenyl-2H-tetrazolium salt];

2,3-diphenyl-5-(4-chlorophenyl) tetrazolium salt;

2,5-diphenyl-3-(p-diphenyl) tetrazolium salt;

2,3-diphenyl-5-(p-diphenyl) tetrazolium salt;

2,5-diphenyl-3-(4-styrylphenyl) tetrazolium salt;

2,5-diphenyl-3-(m-tolyl) tetrazolium salt; and 2,5-diphenyl-3-(p-tolyl) tetrazolium salt.

The tetrazolium compound is not limited to those described above. In addition to the above-mentioned tetrazolium compounds, a tetrazolium compound containing ring substituents having a benzene ring structure at two positions and one ring substituent having a structure other than the benzene ring structure at one position on its tetrazole ring also may be used. Examples of such a tetrazolium compound include:

2,3-diphenyl-5-(2-thienyl) tetrazolium salt;

2-benzothiazoyl-3-(4-carboxy-2-methoxyphenyl)-5-[4-(2-sulfoethyl carbamoyl) phenyl]-2H-tetrazolium salt;

2,2'-dibenzothiazoyl-5,5'-bis [4-di(2-sulfoethyl) carbamoylphenyl]-3,3'-(3,3'-dimethoxy-4,4'-biphenylene) ditetrazolium salt; and 3-(4,5-dimethyl-2-thiazoyl)-2,5-diphenyl-2H-tetrazolium salt.

Further, a tetrazolium compound containing ring substituents having a benzene ring structure at two positions and one substituent not having a ring structure at one position on its tetrazole ring also can be used. Examples of such a tetrazolium compound include:

2,3-diphenyl-5-cyano tetrazolium salt;

2,3-diphenyl-5-carboxy tetrazolium salt;

2,3-diphenyl-5-methyltetrazolium salt; and 2,3-diphenyl-5-ethyl tetrazolium salt.

Among the above-mentioned tetrazolium compounds, the tetrazolium compounds containing three ring substituents are preferable as described above. Among these, the tetrazolium compounds containing three ring substituents having a benzene ring structure and a large number of electron-withdrawing functional groups is more preferable, and 2-(4-iodophenyl)-3-(2,4-dinitrophenyl)-5-(2,4-disulfophenyl)-2H-tetrazolium salt is most preferable. It is to be noted here that the above-mentioned tetrazolium compounds may be a salt or may have been ionized, for example. Further, the tetrazolium compounds may be used alone or in combinations of two or more types.

The surfactant to be used in the method of determining Hb according to the present invention is not specifically limited. However, polyoxyethylene ethers and the like preferably are used, for example. Polyoxyethylene ethers, which are represented by $[C_LH_M{-}O{-}(CH_2CH_2O)_NH]$, are compounds in which a polyoxyethylene chain and a hydrocarbon chain are linked with each other by ether linkage. Examples of the hydrocarbon chain include an alkyl group, an alkyl phenyl group, and the like. Preferably, the polyoxyethylene chain has a weight-average degree of polymerization (N) in the range from 8 to 23 and the hydrocarbon chain has a carbon number (L) in the range from 8 to 18. More preferably, the polyoxyethylene chain has a weight-average degree of polymerization (N) in the range from 8 to 15 and the hydrocarbon chain has a carbon number (L) in the range from 8 to 16. Most preferably, the polyoxyethylene chain has a weight-average degree of polymerization (N) in the range from 8 to 10 and the hydrocarbon chain has a carbon number (L) in the range from 8 to 14. For example, the hydrocarbon chain may be a straight chain or may have a branched chain. Specific examples of the polyoxyethylene ethers include polyoxyethylene-p-t-octylphenyl ether, polyethylene glycol (10) lauryl ether, and polyethylene glycol (9) lauryl ether. The polyoxyethylene ethers may be used alone or in combinations of two or more types.

More specifically, polyoxyethylene-p-t-octylphenyl ether such as commercially available Triton-type surfactants and the like; polyoxyethylene sorbitan alkyl ester such as commercially available Tween-type surfactants and the like; and polyoxyethylene alkyl ether such as commercially available Brij-type surfactants and the like can be used. Other than these, polyoxyethylene (10) lauryl ether; polyoxyethylene (9) lauryl ether such as Nikkol BL-9 EX (trade name, available from Wako Pure Chemical Industries, Ltd.: the weight-average degree of polymerization N of polyoxyethylene is 9) and the like; and polyoxyethylene octylpbenyl ether such as Tergitol NPX (trade name, available from Nacalai Tesque, Inc.: the weight-average degree of polymerization N of polyoxyethylene is about 10.5), Tergitol NP-40 (trade name, available from Nacalai Tesque, Inc.: the weight-average degree of polymerization N of polyoxyethylene is 20), and the like also can be used.

The FAOD to be used in a method of determining a ratio of glycated Hb according to the present invention preferably is the one catalyzing a reaction represented by Formula (1) below.

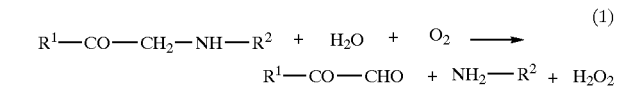

(1)

In Formula (1), $R^1$ denotes a hydroxyl group or a residue derived from a sugar that is not yet subjected to the glycation reaction (i.e., sugar moiety). The sugar moiety ($R^1$) is an aldose residue when the unreacted sugar is aldose, and is a ketose residue when the unreacted sugar is ketose. When the unreacted sugar is glucose, for example, the sugar in the glycated product takes on the fructose structure after the glycation reaction due to Amadori rearrangement. In this case, the sugar moiety ($R^1$) is a glucose residue (aldose residue). This sugar moiety ($R^1$) can be represented, for example, by

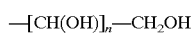

where n denotes an integer of 0 to 6.

In Formula (1), $R^2$ is not specifically limited. However, in the case where the substrate is a glycated amino acid, a glycated peptide, or a glycated protein, $R^2$ varies depending on which of an α-amino group and an amino group other than the α-amino group is glycated.

In Formula (1), in the case where an α-amino group is glycated, $R^2$ is an amino acid residue or a peptide residue represented by Formula (2) below.

(2)

In Formula (2), $R^3$ denotes an amino-acid side chain group. $R^4$ denotes a hydroxyl group, an amino acid residue, or a peptide residue, and can be represented, for example, by Formula (3) below. In Formula (3), n denotes an integer of 0 or more and $R^3$ denotes an amino-acid side chain group as described above.

In Formula (1), in the case where an amino group other than the α-amino group is glycated (i.e., an amino-acid side chain group is glycated), $R^2$ is represented by Formula (4) below.

In Formula (4), $R^5$ denotes a portion other than the glycated amino group in the amino-acid side chain group. For example, in the case where the glycated amino acid is lysine, $R^5$ is as follows.

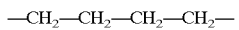

On the other hand, in the case where the glycated amino acid is arginine, for example, $R^5$ is as follows.

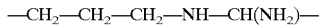

In Formula (4), $R^6$ denotes hydrogen, an amino acid residue, or a peptide residue, and can be represented, for example, by Formula (5) below. In Formula (5), n denotes an integer of 0 or more and $R^3$ denotes an amino-acid side chain group as described above.

In Formula (4), $R^7$ denotes a hydroxyl group, an amino acid residue, or a peptide residue, and can be represented, for example, by Formula (6) below. In Formula (6), n denotes an integer of 0 or more and $R^3$ denotes an amino-acid side chain group as described above.

The protease to be used in the method of determining a ratio of glycated Hb according to the present invention is not specifically limited. Examples of the protease include serine proteases, thiol proteases, metalloproteinases, and the like. More specifically, it is preferable to use a trypsin, proteinase K, chymotrypsin, papain, bromelain, subtilisin, elastase, aminopeptidase, and the like. It is more preferable to use a protease that degrades the glycated Hb selectively, e.g., a bromelain, papain, trypsin derived from porcine pancreas, metalloproteinase, and protease derived from *Bacillus subtilis*. Examples of the protease derived from *Bacillus subtilis* include Protease N (trade name, available from Fluka Chemie AG, for example), Protease N "AMANO" (trade name, available from Amano Enzyme Inc.), and the like. Examples of the metalloproteinase include the metalloproteinase (EC 3. 4. 24. 4) derived from the genus Bacillus (e.g., available from Toyobo Co., Ltd. under the trade name Toyoteam) and the like. Among these, a metalloproteinase, bromelain, and papain are more preferable, and a metalloproteinase is most preferable. By using the protease that degrades the glycated Hb selectively, a degradation product of glycated Hb can be prepared selectively, thereby allowing the accuracy of determination to be further improved.

Hereinafter, a method of determining Hb according to the present invention will be described by taking as an example the case where whole blood is used as a sample.

First, a hemolysate sample is prepared by causing hemolysis of whole blood or of a blood cell fraction separated from the whole blood according to a usual method such as centrifugation and the like. The method of causing hemolysis is not specifically limited, and can be, for example, a method using a surfactant, a method using ultrasonic waves, and a method utilizing the difference in osmotic pressure. Among these, the method using a surfactant is preferable.

The surfactant to be used for causing hemolysis is not specifically limited. For example, as the surfactant, nonionic surfactants such as polyoxyethylene-p-t-octylphenyl ether (Triton-type surfactant etc.), polyoxyethylene sorbitan alkyl ester (Tween-type surfactant etc.), polyoxyethylene alkyl ether (Brij-type surfactant etc.), and the like can be used. More specifically, Triton X-100 (trade name), Tween-20 (trade name), Brij 35 (trade name), and the like can be used, for example. Generally, the treatment with the surfactant can be carried out under the following conditions: in the case where the solution to be treated contains 1 to 10 vol % of blood cells, the surfactant is added to the solution so as to give a concentration of 0.1 to 1 wt % and the resultant mixture is stirred at room temperature for about 5 seconds to 1 minute.

Further, when utilizing the difference in osmotic pressure, to the whole blood was added 2 to 100 times its volume of purified water to cause hemolysis, for example.

Next, the tetrazolium compound is added to the hemolysate sample to denature the Hb.

The tetrazolium compounds as described above can be used as the tetrazolium compound. The tetrazolium compound is added to the sample at the following ratio, for example: in the case where the hemolysate sample contains 0.2 to 2 vol % of blood cells, the tetrazolium compound preferably is added to the sample so as to give a concentration in the range from 0.005 to 400 mmol/L, more preferably from 0.02 to 100 mmol/L, and most preferably from 0.1 to 50 mmol/L. More specifically, in the case where the tetrazolium compound is 2-(4-iodophenyl)-3-(2,4-dinitrophenyl)-5-(2,4-disulfophenyl)-2H-tetrazolium salt, the tetrazolium compound preferably is added to the sample so as to give a concentration in the range from 0.004 to 16 mmol/L, more preferably from 0.02 to 10 mmol/L, and most preferably from 0.1 to 5 mmol/L.

The tetrazolium compound may be used as it is. However, on account of the ease of operation, treatment efficiency, and the like, it is preferable to use a tetrazolium compound solution obtained by dissolving the tetrazolium compound in a solvent. The concentration of the tetrazolium compound in the solution can be decided as appropriate depending on the type of the tetrazolium compound (e.g., the molecular weight thereof and the like. For example, the concentration of the tetrazolium compound in the solution is in the range from 0.01 to 120 mmol/L, preferably from 0.1 to 50 mmol/L, and more preferably from 0.2 to 20 mmol/L. As the solvent, distilled water, a physiological salt solution, buffers, and the like can be used, for example. Examples of the buffer includes an MES buffer, MOPS buffer, phosphate buffer, ADA buffer, PIPES buffer, ACES buffer, CHES buffer, HEPES buffer, and the like. The pH of the buffer preferably is in the range from 5.5 to 10.0.

The conditions of the treatment with the tetrazolium compound are not specifically limited. For example, the treatment with the tetrazolium compound is carried out under the following conditions: the temperature in the range from 4° C. to 50° C. and the treatment time in the range from 20 seconds to 60 minutes; preferably, the temperature in the range from 15° C. to 40° C. and the treatment time in the range from 20 seconds to 20 minutes; and more preferably, the temperature in the range from 25° C. to 37° C. and the treatment time in the range from 30 seconds to 6 minutes.

Further, by carrying out the treatment with the tetrazolium compound in the presence of the surfactant as described above, the denaturation of the Hb can be accelerated further. Thus, on account of the ease of operation and the like, the tetrazolium compound may be added to the sample previously during the treatment for causing hemolysis.

The amount of the surfactant added to the sample is not specifically limited. For example, the surfactant may be added to the sample at the following ratio: in the case where the hemolysate sample contains 0.2 to 1 vol % of blood cells, the surfactant preferably is added to the solution so as to give a concentration in the range from 0.05 to 50 mmol/L, more preferably from 0.2 to 30 mmol/L, and most preferably from 0.3 to 10 mmol/L. More specifically, in the case where the surfactant is Triton X-100 (trade name), the surfactant preferably is added to the solution so as to give a concentration in the range from 0.2 to 100 mmol/L, more preferably from 1 to 30 mmol/L, and most preferably from 2 to 20 mmol/L. On the other hand, in the case where the surfactant is Brij 35 (trade name), the surfactant preferably is added to the solution so as to give a concentration in the range from 0.1 to 50 mmol/L, more preferably from 0.5 to 20 mmol/L, and most preferably from 1 to 10 mmol/L.

The surfactant may be added to the sample so that a content of the surfactant per mole of the tetrazolium compound is in the range from 0.01 to 70 mol, more preferably from 0.05 to 50 mol, and most preferably from 0.1 to 20 mol, for example.

More specifically, in the case where the surfactant is Triton X-100 (trade name), the surfactant is added to the sample so that a content of the surfactant per millimole of the tetrazolium compound is in the range from 0.05 to 15 mmol, more preferably from 0.1 to 10 mmol, and most preferably from 0.2 to 5 mmol. On the other hand, in the case where the surfactant is Brij 35 (trade name), the surfactant is added to the sample so that a content of the surfactant per millimole of the tetrazolium compound is in the range from 0.05 to 10 mmol, more preferably from 0.1 to 8 mmol, and most preferably from 0.2 to 4 mmol. The surfactant may be added to the sample previously during the treatment for causing hemolysis so as to give a sufficient surfactant concentration for accelerating the denaturation of the Hb.

Next, an absorbance of the denatured Hb is measured. The absorbance of the denatured Hb preferably is measured at a wavelength in the range from 440 to 700 nm, more preferably from 500 to 670 nm, and most preferably from 540 to 670 nm. Further, in the case where the dual-wavelength measurement is carried out using the wavelength in the above-mentioned range as the main wavelength, the sub-wavelength preferably is in the range from 730 to 900 nm, more preferably from 800 to 900 nm, and most preferably from 800 to 850 nm.

Thereafter, the amount of the Hb is determined using the absorbance thus measured and a calibration curve prepared in advance. As described above, by denaturing the Hb in the sample with the tetrazolium compound, the amount of the Hb can be determined easily and accurately as the amount of the denatured Hb.

The preparation of a calibration curve can be carried out as follows, for example: first, samples containing Hb at various concentrations are provided; Hb concentrations of these samples are determined by the method of determining Hb according to the present invention and a know method of determining Hb; and then a calibration curve is prepared based on the values obtained. The known method is not specifically limited as long as it can determine Hb with high accuracy. However, the HiCn method as an international standard method is preferable, for example. It is also possible to prepare a calibration curve as follows: first, a standard sample with a known Hb concentration is provided; a Hb concentration of this standard sample is determined by the method of determining Hb according to the present invention; and then a calibration curve is prepared based on the value obtained and the known Hb concentration.

Next, with regard to a method of determining a ratio of glycated Hb according to the present invention, one example of the first method employing the whole blood as a sample will be described.

First, a hemolysate sample is prepared and treated with a tetrazolium compound, and the absorbance of the denatured Hb is measured to determine an amount of the Hb, in the same manner as described above.

Then, the hemolysate sample that has been treated with the tetrazolium compound is treated with a protease to degrade the denatured Hb. This protease treatment is carried out because the FAOD to be added in a subsequent treatment acts on a glycated amino acid and a glycated peptide fragment shorter than a glycated protein and a glycated peptide more easily than on the glycated protein and the glycated peptide.

In the case where the hemolysate sample is treated using a papain as the protease, the treatment generally is carried out under the following conditions: the protease concentration in the reaction solution in the range from 100 to 30,000 U/L; the blood cell concentration in the reaction solution in the range from 0.07 to 12 vol % or the Hb concentration in the reaction solution in the range from 0.1 to 10 g/L; the reaction temperature in the range from 15° C. to 60° C.; the reaction time in the range from 10 minutes to 40 hours; and the pH in the range from 5 to 9. Further, the type of the buffer is not specifically limited, and can be, for example, Tris-HCl buffer, EPPS buffer, PIPES buffer, phosphate buffer, ADA buffer, citrate buffer, acetate buffer, and the like.

In the case where the hemolysate sample is treated using a metalloproteinase as the protease, the treatment generally is carried out under the following conditions: the protease concentration in the reaction solution in the range from 10 to 10,000 KU/L; the blood cell concentration in the reaction solution in the range from 0.07 to 12 vol % or the Hb concentration in the reaction solution in the range from 0.1 to 10 g/L; the reaction temperature in the range from 15° C. to 60° C., the reaction time in the range from 10 minutes to 40 hours; and the pH in the range from 6 to 9. As the buffer, the above-mentioned various buffers also can be used. Further, other proteinases also can be used.

Next, the degradation product of the denatured Hb obtained through the above-mentioned protease treatment is treated with FAOD. This FAOD treatment catalyzes the reaction represented by Formula (1) above.

Similarly to the above-mentioned protease treatment, this FAOD treatment preferably is carried out in a buffer. The conditions of the FAOD treatment are decided as appropriate depending on the type of the FAOD to be used, the concentration of the glycated Hb to be determined, and the like.

More specifically, the FAOD treatment is carried out, for example, under the following conditions: the FAOD concentration in the reaction solution in the range from 50 to 50,000 U/L, the blood cell concentration in the reaction solution in the range from 0.01 to 1 vol %, the reaction temperature in the range from 15° C. to 37° C., the reaction time in the range from 1 to 60 minutes, and the pH in the range from 6 to 9. The type of the buffer is not specifically limited, and the same buffers as used in the protease treatment also can be used in the FAOD treatment.

Subsequently, POD and the color-developing substrate are added to the hemolysate sample so that a redox reaction is caused by the POD between the hydrogen peroxide generated by the FAOD treatment and the color-developing substrate.

As the color-developing substrate, N-(carboxymethylaminocarbonyl)-4,4'-bis(dimethylamino) diphenylamine sodium, orthophenylenediamine (OPD), a substrate obtained by combining a Trinder's reagent and 4-aminoantipyrine, and the like can be used, for example. Examples of the Trinder's reagent include phenols, phenol derivatives, aniline derivatives, naphthols, naphthol derivatives, naphthylamine, naphthylamine derivatives, and the like. Further, in place of the above-mentioned 4-aminoantipyrine, it is possible to use aminoantipyrine derivatives, vanillin diamine sulfonic acid, methyl benzothiazolinone hydrazone (MBTH), sulfonated methyl benzothiazolinone hydrazone (SMBTH), and the like. Among these color-developing substrates, N-(carboxymethylaminocarbonyl)-4,4'-bis (dimethylamino) diphenylamine sodium is most preferable as described above.

The above-mentioned redox reaction generally is induced in a buffer under the conditions decided as appropriate depending on the concentration of the hydrogen peroxide generated and the like. Generally, the redox reaction is induced under the following conditions: the POD concentration in the reaction solution in the range from 10 to 20,000 IU/L, the concentration of the color-developing substrate in the range from 0.0001 to 1 mmol/l, the reaction temperature in the range from 20° C. to 37° C., the reaction time in the range from 1 to 5 minutes, and the pH in the range from 6 to 9. Further, the buffer is not specifically limited, and the same buffers as used in the protease treatment, the FAOD treatment, etc. also can be used.

After the color-developing substrate has developed color as a result of the redox reaction, the degree of color development (i.e., the absorbance) of the reaction solution is measured with a spectrophotometer. From the thus-measured absorbance and the calibration curve, the amount of the glycated Hb can be known directly, or indirectly using the amount of the hydrogen peroxide.

The wavelength for measuring the absorbance is not specifically limited and can be decided as appropriate depending on the type of the color-developing substrate. However, it is preferable that the absorbance of the color-developing substance is measured at a wavelength in the range from 650 to 900 nm, more preferably from 650 to 800 nm, and most preferably from 650 to 760 nm. Further, in the case where the dual-wavelength measurement is carried out using the wavelength in the above-mentioned range as the main wavelength, the sub-wavelength preferably is in the range from 730 to 900 nm, more preferably from 800 to 900 nm, and most preferably from 800 to 850 nm. Generally, the sub-wavelength is set to be greater than the main wavelength. More specifically, it is preferable that the sub-wavelength is greater than the main wavelength by at least 30 nm, more preferably by at least 50 nm.

More specifically, in the case where N-(carboxymethylaminocarbonyl)-4,4'-bis(dimethylamino) diphenylamine sodium is used as the color-developing substrate, the color-developing substrate preferably is measured at a wavelength in the range from 650 to 760 nm, more preferably from 690 to 760 nm. Further, when the dual-wavelength measurement is carried out using the wavelength in the above-mentioned range as the main wavelength, the sub-wavelength preferably is in the range from 800 to 900 nm, more preferably from 800 to 850 nm.

In the method of determining a ratio of glycated Hb according to the present invention, it is preferable that the wavelength for measuring the denatured Hb and the wavelength for measuring the color-developing substrate are different from each other. Further, in the case where the absorbance of the color-developing substrate is measured by the dual-wavelength measurement, it is preferable that the main wavelength and sub-wavelength are in the ranges where the denatured Hb exhibits no absorption. Further, if an absorbance of the denatured Hb is measured at the wavelength for measuring the color-developing substrate before causing the color-developing reaction and an absorbance obtained after the color-developing reaction is corrected with this absorbance, the accuracy of determination can be further improved.

On the other hand, the wavelength for measuring the denatured Hb and the wavelength for measuring the color-developing substrate may be the same. In this case, the measured value obtained after the Hb is denatured with the tetrazolium compound is regarded as the absorbance of the denatured Hb, and the measured value obtained after the color-developing reaction is corrected with the absorbance of the denatured Hb. That is, the absorbance of the substrate that has developed color can be obtained by subtracting the absorbance of the denatured Hb from the absorbance obtained after the color-developing reaction.

In the case where both the denatured Hb and the color-developing substrate are measured at the same wavelength as described above, the wavelength preferably is in the range from 440 to 700 nm, more preferably from 500 to 670 nm, and most preferably from 540 to 670 nm, for example.

Thereafter, an amount of the glycated Hb is determined using the thus-obtained absorbance and the calibration curve prepared in advance. Then, from the amount of the glycated Hb and the above-mentioned amount of the Hb, the ratio of the glycated Hb is calculated.

The calibration curve can be prepared as follows, for example: first, with respect to a standard sample containing a known amount of glycated Hb, an absorbance is measured after the color-developing reaction according to the method of determining a ratio of glycated Hb of the present invention; and the calibration curve is prepared based on the thus-obtained absorbance and the known amount of the glycated Hb.

It is to be noted here that the amount of the hydrogen peroxide can be determined not only by the above-mentioned enzymic method using the POD etc. but also by an electrical method, for example.

As described above, by denaturing the Hb in the sample with the tetrazolium compound and determining the amount of the denatured Hb, it becomes possible to determine the amount of the Hb and the amount of the glycated Hb in a series of operations. Therefore, a ratio of glycated Hb can be determined quickly and simply. Moreover, because the tetrazolium compound is added to the sample in advance, the effect of various reducing substances present in the sample on the redox reaction can be eliminated, thereby allowing the accuracy of determination to be further improved.

In the case where Hb to be determined is human Hb, the ratio of glycated Hb is referred to as HbA1c %, for example. Thus, a method of determining a ratio of glycated Hb according to the present invention is useful for determining HbA1c %.

Next, with regard to a method of determining a ratio of glycated Hb according to the present invention, one example of the second method employing the whole blood as a sample will be described.

The hemolysate sample is treated with a tetrazolium compound in the same manner as described above to denature the Hb contained therein. After the sample is treated with a protease, the sample is further treated with FAOD. Thereafter, the determination of the denatured Hb and the measurement of the degree of color development (i.e., the absorbance) with a spectrophotometer can be performed with respect to this reaction solution.

In this case, it is necessary that the wavelength for measuring the denatured Hb and the wavelength for measuring the color-developing substrate are different from each other because the determinations of the denatured Hb and the degree of color development are carried out with respect to the same reaction solution. For example, the wavelength (A) for measuring the denatured Hb is in the range from 440 to 700 nm and the wavelength (B) for measuring the degree of color development is in the range from 500 to 800 nm; preferably, the wavelength (A) is in the range from 500 to 670 nm and the wavelength (B) is in the range from 540 to 670 nm; and more preferably, the wavelength (A) is in the range from 540 to 670 nm and the wavelength (B) is in the range from 540 to 670 nm. Further, it is preferable that the distance between the wavelength (A) and the wavelength (B) is at least 30 nm, for example.

Further, when carrying out the dual-wavelength measurement, the main wavelength and the sub-wavelength of the wavelengths (A) and (B) may be as follows, for example: preferably, (A) the main wavelength in the range from 440 to 700 nm and the sub-wavelength in the range from 730 to 900 nm, (B) the main wavelength in the range from 500 to 800 nm and the sub-wavelength in the range from 800 to 900 nm; more preferably, (A) the main wavelength in the range from 500 to 670 nm and the sub-wavelength in the range from 730 to 900 nm, (B) the main wavelength in the range from 540 to 750 nm and the sub-wavelength in the range from 800 to 900 nm; and most preferably, (A) the main wavelength in the range from 540 to 670 nm and the sub-wavelength in the range from 800 to 850 nm, (B) the main wavelength in the range from 540 to 750 nm and the sub-wavelength in the range from 800 to 850 nm.

EXAMPLES

Hereinafter, examples of the present invention will be described.

Example 1

In Example 1, a Hb concentration was determined by denaturing Hb in blood cells with a tetrazolium compound and measuring an absorbance of the denatured Hb, and the correlation between the thus-determined Hb concentration and the Hb concentration determined according to HiCN method as an international standard method was examined. The samples, reagents, and method used in the present example will be described in the following.

Preparation of Samples

Whole blood collected from healthy subjects and diabetic subjects was centrifuged (2000 G, 3 min), and blood cells and plasma were separated and collected from the whole blood. Then, the blood cells and the plasma were mixed with each other at predetermined ratios (blood cells:plasma=10:0, 9:1, 8:2, 7:3, 6:4, 5:5, and 4:6). After that, the mixtures were diluted 15-fold (by volume) with a 0.4 wt % aqueous solution of Triton X-100 (trade name, available from Wako Pure Chemical Industries, hereinafter the same) to prepare 45 samples in total.

Standard Solutions

Hemocon N (trade name, available from AZWELL Inc.) was dissolved in a 2.4 wt % aqueous solution of Triton X-100 (trade name) so as to give predetermined Hb concentrations (0, 50, 100, 200, 300 g/L). The resultant solutions were used as standard solutions.

WST-3 Solution: hereinafter the same 2-(4-iodophenyl)-3-(2,4-dinitrophenyl)-5-(2,4-disulfophenyl)-2H-tetrazolium monosodium salt (the trade name WST-3: available from Dojindo Laboratories, hereinafter the same) represented by Formula (7) below was dissolved in purified water so as to give a concentration of 1.66 mM to prepare a WST-3 solution.

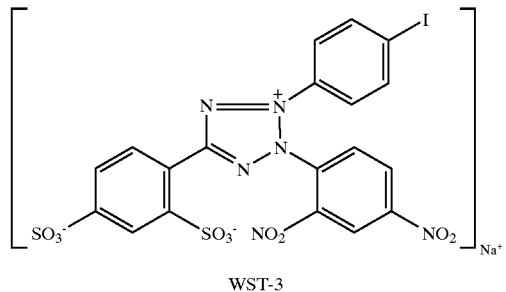

WST-3

Buffer 0.1 mM CHES buffer (pH 9.0)

Determining Method

The above-mentioned respective samples were diluted 3-fold with purified water, and 15 μL of the CHES buffer was mixed with 25 μL of the respective diluted solutions. Thereafter, 45 μL of the WST-3 solution was added to the respective mixtures. After the mixtures were incubated at 37° C. for 5 minutes, the absorbance of the mixtures was measured at the main wavelength of 596 nm and the sub-wavelength of 884 nm using a biochemical automatic analysis apparatus (the trade name JCA-BM 8: available from Japan Electron Optics Laboratory Co. Ltd., hereinafter the same). The absorbance thus measured hereinafter is referred to as "the absorbance by the WST-3 method". Further, as a control, the Hb concentration of the samples was determined according to the HiCN method using Hemoglobin Test Wako (trade name, available from Wako Pure Chemical Industries, Ltd.). The Hb concentration thus determined hereinafter is referred to as "the Hb concentration by the HiCN method".

On the other hand, with respect to the above-mentioned standard solutions, the absorbance by the WST-3 method was determined, and a calibration curve showing the relationship between the absorbance and the Hb concentration was prepared. The calibration curve obtained is represented by the following equation.

$$y = 505.1x - 6.1692$$

y: Hb concentration (g/L)

x: absorbance obtained by WST-3 method

Then, the absorbance by the WST-3 method of the samples were substituted into the calibration curve to determine the Hb concentration of the samples. The Hb concentration obtained using this calibration curve and the Hb concentrations by the HiCN method of the samples are shown in the graph of FIG. 1.

FIG. 1 is a graph showing the correlation between the Hb concentration (g/L) obtained using the calibration curve and the Hb concentration by the HiCN method. The correlation equation had a gradient of "0.9733". The fact that the correlation equation had a gradient close to "1" demonstrates that the determining method according to Example 1 can determine a Hb concentration with accuracy comparable to that of the HiCN method as a control. Furthermore, from the fact that the correlation coefficient was r=0.9978, it is understood that the Hb concentration can be determined stably with high accuracy.

Example 2

In Example 2, the amount of Hb was determined by the method of determining Hb according to the present invention, and the correlation between the thus-determined amount of Hb and the amount of Hb determined by the SLS method as a control was examined. The samples, reagents, determining method, etc. used in the present example will be described in the following.

(Hemolysate Reagent)

| | |
|---|---|
| TAPS (Dojindo Laboratories) | 140 mmol/L |
| glycinamide (Nacalai Tesque, Inc.) | 60 mmol/L |
| polyoxyethylene lauryl ether (Nacalai Tesque, Inc.) | 24 g/L |
| (First Reagent: pH 5.5) | |
| MES (Dojindo Laboratories) | 5 mmol/L |
| WST-3 | 2 mmol/L |
| sodium azide (Nacalai Tesque, Inc.) | 0.05 g/L |
| $CaCl_2$ (Nacalai Tesque, Inc.) | 5 mmol/L |
| NaCl (Nacalai Tesque, Inc.) | 150 mmol/L |
| metalloproteinase (trade name Toyoteam: Toyobo Co., Ltd.) | 3 g/L |
| (Second Reagent: pH 6.9) | |
| FAOD (ARKRAY, INC.) | 26 KU/L |
| POD (Toyobo Co., Ltd.) | 78 KU/L |
| DA-64 (Wako Pure Chemical Industries, Ltd.) | 0.052 mmol/L |
| Tris-HCl (Nacalai Tesque, Inc.) | 200 mmol/L |

Samples

Whole blood collected from healthy subjects and diabetic subjects (71 subjects in total) was centrifuged (1000 G, 10 min), and blood cells fractions were collected. To 10 µL of the respective blood cell fractions was added 40 µL of the hemolysate reagent to prepare hemolysate samples (hereinafter the same).

Determining Method

10 µL of purified water was added to 10 µL of the above-mentioned respective hemolysate samples, and thereafter, 65 µL of the first regent was further added. The resultant mixtures were incubated at 37° C. (the amount of the reaction solutions: 85 µL). Then, 4.5 minutes after the start of the incubation, the absorbance of the reaction solutions was measured at the predetermined wavelength (545 nm, 571 nm, 596 nm, 658 nm, 694 nm, and 751 nm) using the above-mentioned biochemical automatic analysis apparatus. The measured value obtained was hereinafter referred to as the "first absorbance".

Then, 5 minutes after the start of the incubation, 45 µL of the second reagent was added to the respective reaction solutions. The resultant mixtures were incubated at 37° C. for 3 minutes (the amount of the reaction solutions: 130 µL). Then, the absorbance of the reaction solutions was measured at the predetermined wavelength (545 nm, 571 nm, and 596 nm) using the above-mentioned biochemical automatic analysis apparatus. The measured value obtained was hereinafter referred to as the "second absorbance".

On the other hand, as a control, Hb was determined according to the above-mentioned SLS method. First, 4 µL of purified water was added to 4 µL of the same hemolysate samples as in Example 2, and thereafter, 100 µL of a SLS method reagent shown below was further added. The resultant mixtures were incubated at 37° C. for 5 minutes. Then, 5 minutes after the start of the incubation, the absorbance of the reaction solutions was measured at the wavelength of 545 nm using the above-mentioned biochemical automatic analysis apparatus.

(SLS Method Reagent)

| | |
|---|---|
| SLS | 0.64 g |
| Triton X-100 | 0.75 g |
| Potassium phosphate buffer (pH 7.2) | 1.0 L |

The first and second absorbances obtained by the method of the present example and the absorbances obtained by the SLS method as a control with respect to all the samples (71 subjects) were plotted (not shown) to determine the correlation coefficient between the present example and the control. The results are shown in Table 1 below.

TABLE 1

| measurement wavelength | correlation coefficient in 1st absorbance measurement | correlation coefficient in 2nd absorbance measurement |
|---|---|---|
| 545 nm | 0.993 | 0.993 |
| 571 nm | 0.993 | 0.993 |
| 596 nm | 0.993 | 0.989 |
| 658 nm | 0.993 | — |
| 694 nm | 0.993 | — |
| 751 nm | 0.916 | — |

As described above, according to the method of determining Hb according to the present invention, it is possible to carry out the determination showing a high correlation with the determination according to the SLS method. In addition, the absorbance of the denatured Hb could be measured accurately not only when the measurement was carried out immediately after the Hb had been denatured with the first reagent but also when the measurement was carried after the color-developing reaction was induced by the second reagent.

Example 3

In Example 3, HbA1c % was determined by the method of determining a ratio of glycated Hb according to the present invention, and the correlation between the HbA1c % thus determined and the HbA1c % determined according to a control method was examined.

With respect to the above-mentioned hemolysate samples (71 subjects in total), measurement of a first absorbance (measurement wavelength: 571 nm) and measurement of a second absorbance (measurement wavelength: 751 nm) were carried out in the same manner as in Example 2. On the other hand, using a standard solution with known amounts of Hb and HbA1c, a calibration curve (Hb calibration curve) showing the relation between the first absorbance obtained by the method of the present invention and the known amount of Hb, and a calibration curve (HbA1c calibration curve) showing the relationship between the second absorbance obtained by the method of the present invention and the known amount of HbA1c were prepared.

Subsequently, the first absorbance was substituted into the Hb calibration curve to determine the amount of Hb in the samples, and the second absorbance was substituted into the HbA1c calibration curve to determine the amount of HbA1c in the samples. Then, HbA1c % was determined by substituting the amount of Hb and the amount of HbA1c into the following equation.

HbA1c %=(HbA1c amount/Hb amount)×100

As a control, with respect to the same hemolysate samples (71 subjects), the amount of Hb was determined by the SLS method, and HbA1c % was determined using RAPIDIA Auto HbA1c (trade name, available from SRL, Inc.). Then, the correlation coefficient between the amount of Hb obtained by the method of the present example and the amount of Hb obtained by the control method, and the correlation coefficient between the HbA1c % obtained by the method of the present example and the HbA1c % obtained by the control method were determined.

As a result, the correlation coefficient with regard to the amount of Hb was 0.994, and the correlation coefficient with regard to HbA1c % was 0.9841. These results demonstrate that both the method of determining Hb and the method of determining a ratio of glycated Hb according to the present invention can achieve a remarkably high accuracy of determination.

Example 4

In Example 4, HbA1c % was determined by the method of determining a ratio of glycated Hb according to the present invention, and the correlation between the HbA1c % thus determined and the HbA1c % determined according to a control method was examined.

With respect to the above-mentioned hemolysate samples (71 subjects in total), measurement of a first absorbance and measurement of a second absorbance (hereinafter, referred to as "absorbance before correction") were carried out in the same manner as in Example 2. The measurement of the first absorbance was carried out at the wavelengths of 569 nm, 658 nm, 694 nm, and 751 nm, and the absorbance obtained in this measurement was regarded as the absorbance of denatured Hb. On the other hand, the measurement of the second absorbance was carried out at the wavelengths of 569 nm, 658 nm, 694 nm, and 751 nm.

As described above, according to the results of Example 3, the correlation coefficient between the HbA1c % obtained when the second absorbance was measured at the wavelength of 751 nm and the HbA1c % obtained by the control method was as high as 0.9841. Thus, it can be said that the results of Example 3 demonstrate that the amount of HbA1c can be determined with high accuracy when the absorbance measurement was carried out at a wavelength of 751 nm. Accordingly, using the second absorbance measured at the wavelength of 751 nm as a criterion for evaluating the accuracy for determination, the correlation coefficient between the second absorbance measured at the wavelength of 751 nm and the second absorbance measured at each wavelength was determined.

Further, based on the following equation, the second absorbance was corrected using the first absorbance obtained at the corresponding wavelength (the corrected absorbance is hereinafter referred to as "absorbance after correction"). The results are shown in Table 2 below.

absorbance after correction=$A2-(A1\times85/130)$

A1: first absorbance
A2: second absorbance

TABLE 2

| measurement wavelength | correlation coefficient | |
|---|---|---|
| | absorbance before correction | absorbance after correction |
| 596 nm | — | 0.9474 |
| 658 nm | 0.9785 | 0.9998 |
| 694 nm | 0.9998 | 1.0 |
| 751 nm | 1.0 | 1.0 |

As can be seen from the results, the absorbances obtained at the respective wavelengths exhibited high correlations with the absorbance obtained at 751 nm, and the correlation coefficients were improved further by making the correction. Further, the results of Example 2 revealed that the amount of Hb could be determined with high accuracy. Therefore, from the results of Example 2 and the present example, it is understood that the method of determining a ratio of glycated Hb according to the present invention can determine HbA1c % with high accuracy. Besides, the absorbance of the denatured Hb and the absorbance of the glycated Hb may be measured at the same wavelength if the correction is made in the above-mentioned manner. By measuring the absorbance of both the denatured Hb and the glycated Hb at the same wavelength, the condition setting of the measuring apparatus can be carried out easily, for example, and the determination of the ratio of glycated Hb can be carried out simply and quickly.

Industrial Applicability

As specifically described above, according to a method of determining Hb of the present invention, Hb in the sample can be determined easily and accurately without fear of damage to the environment. In addition, when determining a ratio of glycated Hb, even if the sample is treated with a tetrazolium compound according to the method of determining Hb, the tetrazolium compound does not have any effect on the determination of the ratio of glycated Hb utilizing a redox reaction. Therefore, an amount of Hb and an amount of the glycated Hb can be determined in a series of operations simply and with high accuracy. Therefore, by applying the method of determining a ratio of glycated hemoglobin of the present invention utilizing a method of determining Hb of the present invention in the field of clinical tests and the like, for example, the reliability and the importance of glycated Hb as an index for the diagnosis and the like of diabetes further increases.

What is claimed is:

1. A method of determining total hemoglobin in a sample comprising:
    denaturing hemoglobin in a sample with a solution of a tetrazolium compound to give denatured hemoglobin, wherein the pH of the solution is in a range from 5.5 to 10.0;
    measuring an amount of an optical change in the sample at an absorption wavelength specific to the denatured hemoglobin; and
    calculating an amount of the total hemoglobin in the sample from the amount of the optical change.

2. The method according to claim 1,
    wherein the amount of the optical change is an absorbance or a reflectance.

3. The method according to claim 1,
    wherein the amount of the optical change is measured at a wavelength in a range from 440 to 700 nm.

4. The method according to claim 1,
    wherein the tetrazolium compound contains ring substituents at least at two positions on its tetrazole ring.

5. The method according to claim 1,
wherein the tetrazolium compound contains benzene rings at a 2-position and 3-position on its tetrazole ring, and at least one of the benzene rings contains at least one functional group selected from the group consisting of a halogen group, a carboxy group, a nitro group, a hydroxy group, a sulfo group, a methoxy group, and an ethoxy group.

6. The method according to claim 1,
wherein the tetrazolium compound is 2-(4-iodophenyl)-3-(2,4-dinitrophenyl)-5-(2,4-disulfophenyl)-2H-tetrazolium salt.

7. The method according to claim 1,
wherein the tetrazolium compound is added to the sample so that a content of the tetrazolium compound per microliter of the sample is in a range from 0.001 to 100 µmol.

8. The method according to claim 1,
wherein the hemoglobin in the sample is treated with the tetrazolium compound in the presence of a surfactant.

9. The method according to claim 8,
wherein the surfactant is a polyoxyethylene ether.

10. The method according to claim 8,
wherein the surfactant is added to the sample so that a content of the surfactant per mole of the tetrazolium compound is in a range from 0.01 to 70 mol.

11. The method according to claim 1,
wherein the sample contains red blood cells.

12. A method of determining a ratio of glycated hemoglobin to total hemoglobin in a sample comprising:
determining an amount of total hemoglobin in a sample containing glycated hemoglobin by the method according to claim 1;
causing a redox reaction between a glycation site of the denatured hemoglobin obtained and a fructosyl amino acid oxidase;
measuring the degree to which the redox reaction has occurred to determine an amount of the glycated hemoglobin; and
calculating a ratio of the glycated hemoglobin to the total hemoglobin in the sample from the amount of the total hemoglobin and the amount of the glycated hemoglobin.

13. The method according to claim 12,
wherein the denatured hemoglobin is treated with a protease before causing the redox reaction between the glycation site of the denatured hemoglobin and the fructosyl amino acid oxidase.

14. The method according to claim 12,
wherein the redox reaction is caused between the glycation site of the denatured hemoglobin and the fructosyl amino acid oxidase after the amount of the optical change in the sample is measured at the absorption wavelength specific to the denatured hemoglobin.

15. The method according to claim 14,
wherein the amount of the optical change in the sample is measured at the absorption wavelength specific to the denatured hemoglobin, the denatured hemoglobin is then treated with a protease, and thereafter, the redox reaction is caused between a glycation site of a degradation product of the denatured hemoglobin and a fructosyl amino acid oxidase.

16. The method according to claim 14,
wherein the denatured hemoglobin is treated with a protease, the amount of the optical change in the sample is then measured at the absorption wavelength specific to the denatured hemoglobin, and thereafter, a redox reaction is caused between a glycation site of a degradation product of the denatured hemoglobin and a fructosyl amino acid oxidase.

17. The method according to claim 12,
wherein, after the redox reaction is caused between the glycation site of the denatured hemoglobin and the fructosyl amino acid oxidase, the amount of the optical change in the sample is measured at the absorption wavelength specific to the denatured hemoglobin and the redox reaction is determined.

18. The method according to claim 12,
wherein measuring the degree to which the redox reaction has occurred is by measuring an amount of an optical change in a color-developing substance produced by the redox reaction.

19. The method according to claim 18,
wherein the amount of the optical change in the color-developing substance corresponds to an amount of hydrogen peroxide generated by the redox reaction between the glycation site of the denatured hemoglobin and the fructosyl amino acid oxidase.

20. The method according to claim 19,
wherein the color-developing substance is a substrate that develops color by oxidation and has developed color as a result of a reaction caused by an oxidase between the hydrogen peroxide and the substrate.

21. The method according to claim 18,
wherein a wavelength for measuring the color-developing substance is in a range from 650 to 900 nm.

22. The method according to claim 18,
wherein a wavelength for measuring the color-developing substance is the same as that for the step of measuring an amount of an optical change in the sample at an absorption wavelength specific to the denatured hemoglobin.

* * * * *

UNITED STATES PATENT AND TRADEMARK OFFICE
CERTIFICATE OF CORRECTION

PATENT NO. : 6,790,665 B2
DATED : September 14, 2004
INVENTOR(S) : Yonehara et al.

It is certified that error appears in the above-identified patent and that said Letters Patent is hereby corrected as shown below:

Title page,
Insert Item -- [30]     Foreign Application Priorirty Data
          Sep. 28, 2000   (JP)    2000-296540 --

Signed and Sealed this

Twenty-sixth Day of April, 2005

JON W. DUDAS
*Director of the United States Patent and Trademark Office*